US00PP20735P2

(12) United States Plant Patent
Ferguson

(10) Patent No.: US PP20,735 P2
(45) Date of Patent: Feb. 9, 2010

(54) STRAWBERRY PLANT NAMED 'DRISSTRAWEIGHT'

(50) Latin Name: *Fragaria×ananassa*
Varietal Denomination: DrisStrawEight

(75) Inventor: Michael D. Ferguson, Moorpark, CA (US)

(73) Assignee: Driscoll Strawberry Associates, Inc., Watsonville, CA (US)

( * ) Notice: Subject to any disclaimer, the term of this patent is extended or adjusted under 35 U.S.C. 154(b) by 0 days.

(21) Appl. No.: 12/287,322

(22) Filed: Oct. 8, 2008

(51) Int. Cl.
*A01H 5/00* (2006.01)

(52) U.S. Cl. ..... Plt./209

(58) Field of Classification Search ..... Plt./208, Plt./209

See application file for complete search history.

*Primary Examiner*—Susan B McCormick Ewoldt
(74) *Attorney, Agent, or Firm*—Jondle & Associates, P.C.

(57) ABSTRACT

This invention relates to a new and distinct cultivar of strawberry plant named 'DrisStrawEight'. The new cultivar is primarily characterized by its large, firm and medium to strong sweet tasting fruit, medium-vigor and moderate resistance to Powdery mildew, is disclosed.

2 Drawing Sheets

Genus and species: *Fragaria×ananassa.*
Variety denomination: 'DrisStrawEight'.

BACKGROUND OF THE NEW PLANT

The present invention relates to a new and distinct strawberry cultivar designated 'DrisStrawEight' and botanically known as *Fragaria×ananassa*. This new strawberry cultivar was discovered in Camarillo, Calif. in January 2005 and originated from a cross between the female parent 'Driscoll Ojai' (U.S. Plant Pat. No. 18,575) and the male parent 'Driscoll Agoura' (U.S. Plant Pat. No. 15,731). The original seedling of the new cultivar was asexually propagated at a nursery in Shasta County, Calif.

'DrisStrawEight' was subsequently asexually propagated in Shasta County, Calif. and underwent further testing at a nursery in Ventura County, Calif. for three years. The present invention has been found to retain its distinctive characteristics through successive asexual propagations via stolons and tissue culture.

DESCRIPTION OF THE PHOTOGRAPHS

The accompanying color photographs show typical specimens of the new cultivar at various stages of development as nearly true as it is possible to make in color reproductions.

DESCRIPTION OF THE NEW CULTIVAR

Figure 1:
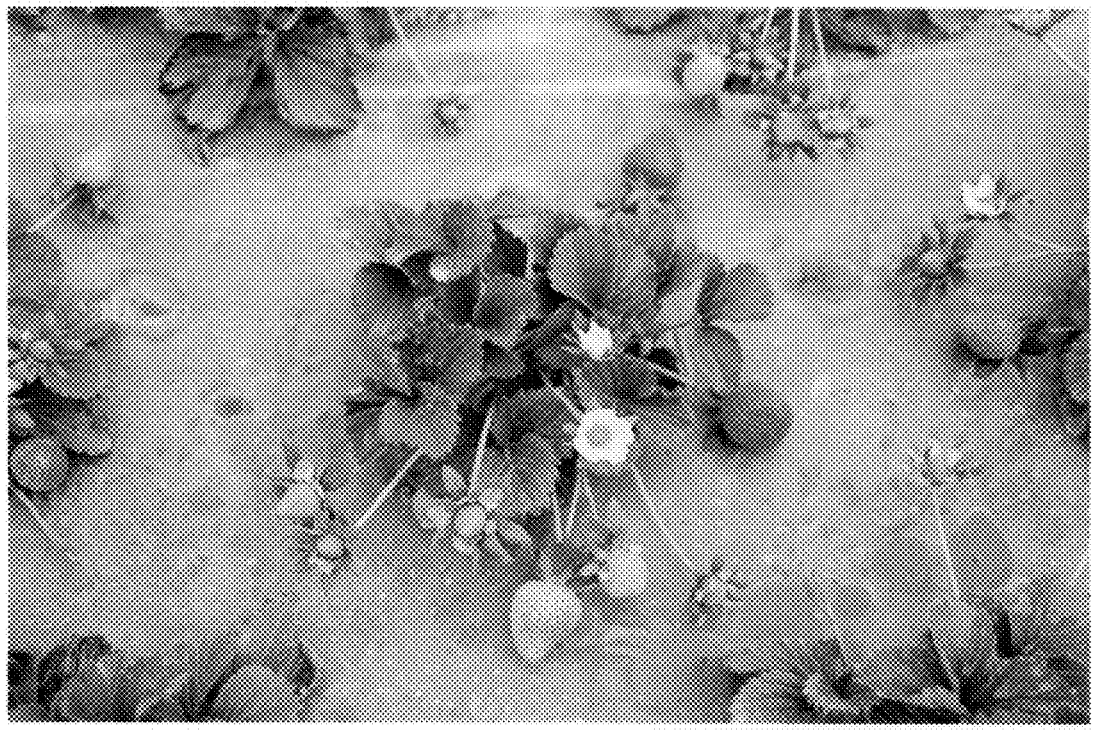
FIG. 1 shows overall plant habit including fruit at various stages of development.
Figure 2:
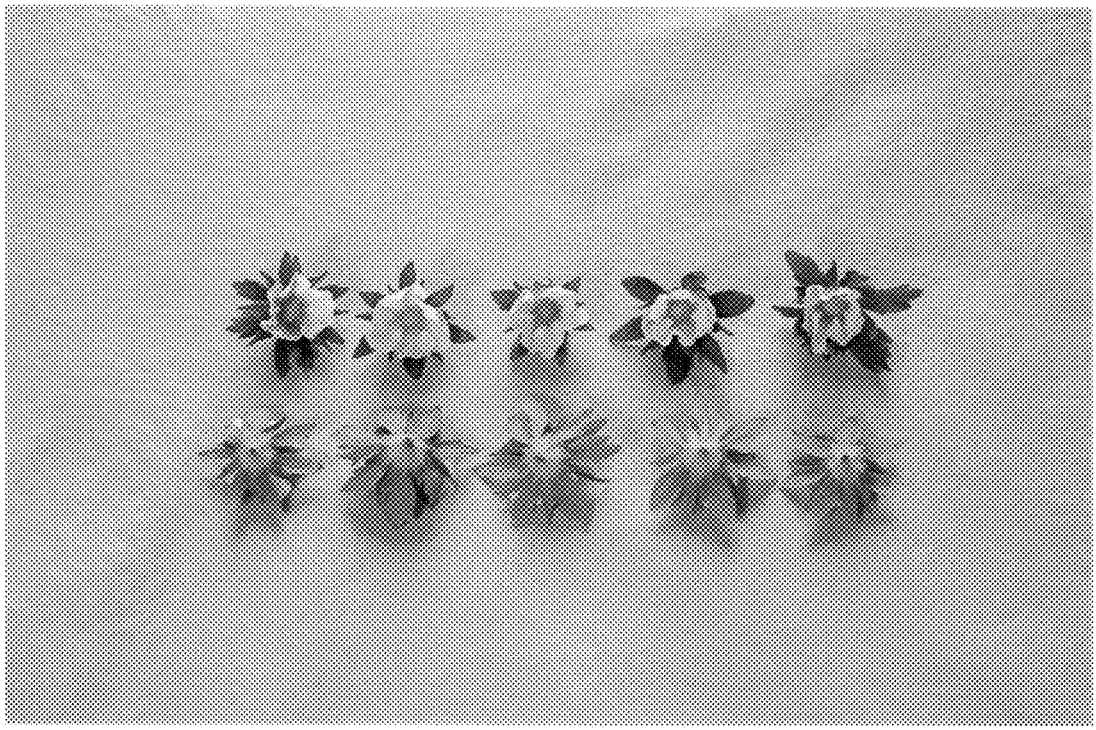
FIG. 2 shows the upper and lower surfaces of several of the flowers.
Figure 3:
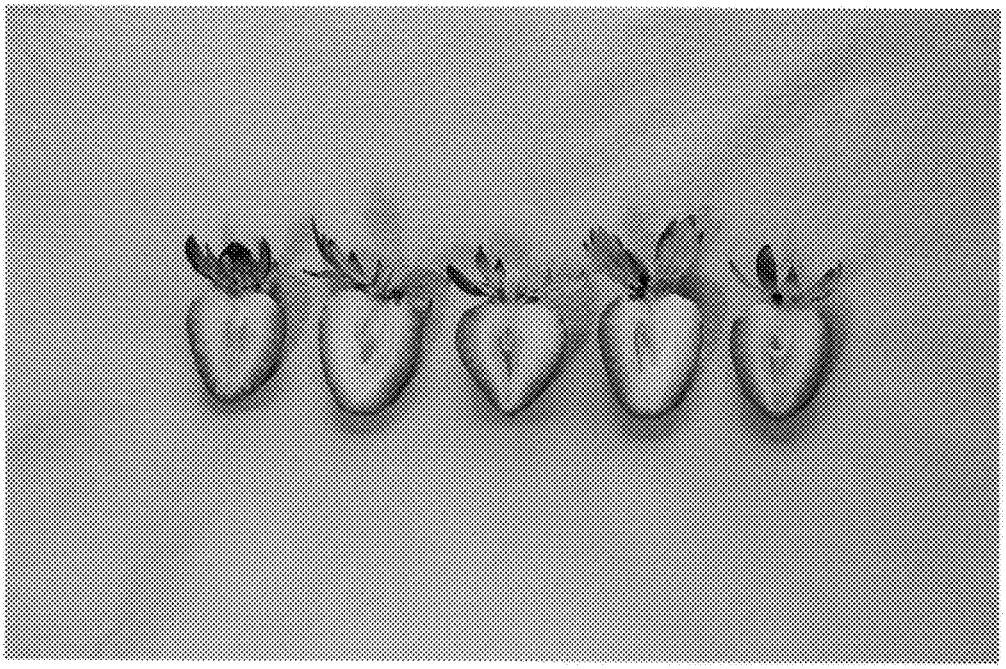
FIG. 3 shows the fruit in longitudinal cross-section.
Figure 4:
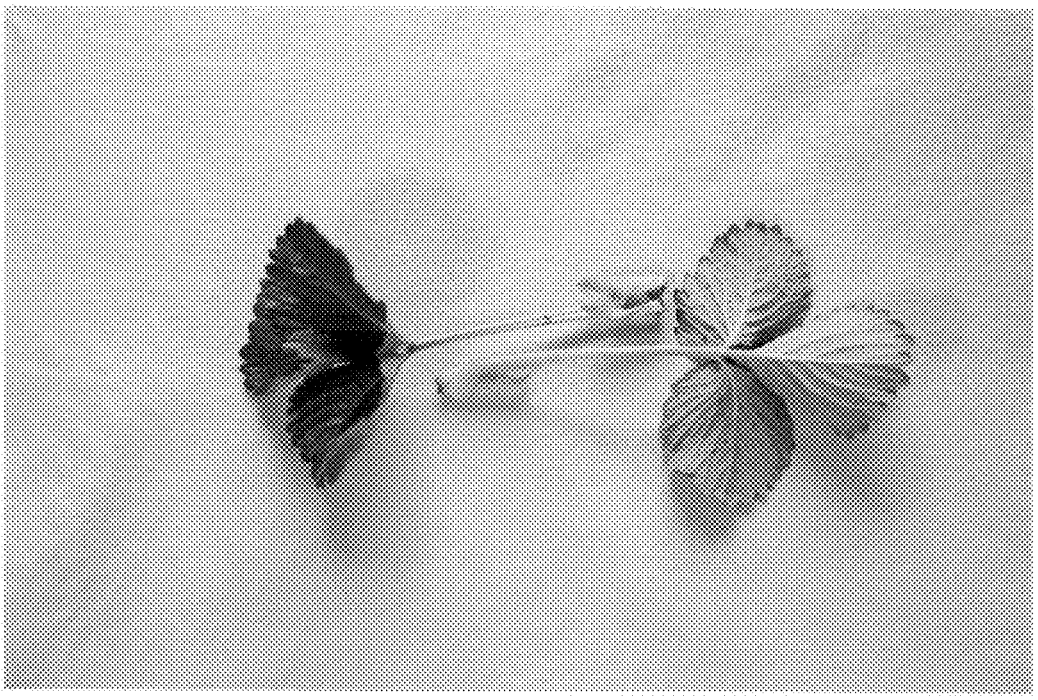
FIG. 4 shows the upper and lower surfaces of the leaves at the three leaf stage.

The following description of 'DrisStrawEight' is based on observations taken in Ventura County, Calif. from 2006–2008. This description is in accordance with UPOV terminology. Color designations, color descriptions, and other phenotypical descriptions may deviate from the stated values and descriptions depending upon variation in environmental, seasonal, climatic and cultural conditions. 'DrisStrawEight' has not been observed under all possible environmental conditions. The botanical description of 'DrisStrawEight' was taken from 6 month-old plants and the botanical descriptions of 'Driscoll Agoura' and 'Driscoll Ojai' were taken from 5 month-old plants. Color terminology follows The Royal Horticultural Society Colour Chart, London (R.H.S.) (2001).

DETAILED BOTANICAL DESCRIPTION

Table 1 shows selected plant characteristics of the new variety compared with plant characteristics of 'Driscoll Agoura' (U.S. Plant Pat. No. 15,731) and 'Driscoll Ojai' (U.S. Plant Pat. No. 18,575). Plant characteristics include stolon number, fruit shape, insertion of achenes and fruit production.

TABLE 1

| Characteristic | 'DrisStrawEight' | 'Driscoll Agoura' | 'Driscoll Ojai' |
|---|---|---|---|
| Stolon number | Medium | Few | Many |
| Fruit shape | Conical and almost cylindrical | Almost cylindrical | Almost cylindrical |
| Insertion of achenes | Below surface | Level with surface | Above surface |
| Fruit production (g/plant) | 529 | 617 | 504 |

Table 2 shows plant characteristics of the new variety compared with plant characteristics of the commercial varieties 'Driscoll Agoura' (U.S. Plant Pat. No. 15,731) and 'Driscoll Ojai' (U.S. Plant Pat. No. 18,575). Plant characteristics include plant height, diameter, the number of crowns per plant, habit, the density of individual plants and the vigor.

TABLE 2

| Characteristic | 'DrisStrawEight' | 'Driscoll Agoura' | 'Driscoll Ojai' |
|---|---|---|---|
| Plant height (cm) | 16.1 | 13.2 | 14.0 |
| Plant diameter (cm) | 28.3 | 30.3 | 32.0 |
| Number of crowns/plant | 2 | 3 | 2 |
| Habit | Globose | Flat | Flat-globose |
| Density of individual plant | Medium | Medium | Medium |
| Vigor | Medium | Weak | Strong |

Table 3 shows leaf characteristics of the new cultivar compared with leaf characteristics of 'Driscoll Agoura' and 'Driscoll Ojai'. Leaf characteristics include terminal leaflet length and width in centimeters, length to width ratio, number of teeth per terminal leaflet, shape of teeth, color of upperside and underside of leaf, leaf shape in cross section, leaf blistering, leaf glossiness, number of leaflets, terminal leaflet margin, terminal leaflet length to width ratio, overall leaf shape and shape of leaf apex and base.

TABLE 3

| Leaf Characteristic | 'DrisStrawEight' | 'Driscoll Agoura' | 'Driscoll Ojai' |
|---|---|---|---|
| Terminal leaflet length (cm) | 0.64 | 0.58 | 0.60 |
| Terminal leaflet width (cm) | 0.61 | 0.56 | 0.63 |
| Terminal leaflet length/width ratio | 1.0 | 1.0 | 1.0 |
| No. teeth/terminal leaflet | 21 | 23 | 20 |
| Shape of teeth | Rounded | Rounded | Rounded |
| Color of upper surface of leaf | RHS 139A (Dark-green) | RHS 139A (Dark-green) | RHS 147A (Medium yellow-green) |
| Color of lower surface of leaf | RHS 148B (Medium yellow-green) | RHS 147B (Medium yellow-green) | RHS 147C (Medium yellow-green) |
| Leaf shape in cross section | Concave | Concave | Concave |
| Leaf blistering | Weak | Medium | Medium |
| Leaf glossiness | Weak | Medium | Medium |
| No. leaflets | Three only | Three only | Three only |
| Terminal leaflet margin | Revolute | Revolute | Revolute to flat |
| Terminal leaflet: length/width ratio | As long as broad | As long as broad | As long as broad |
| Terminal leaflet shape | Orbicular | Orbicular | Orbicular |
| Terminal leaflet base shape | Obtuse | Obtuse | Obtuse |
| Terminal leaflet apex shape | Rounded | Rounded | Rounded |

Table 4 shows information about the petiole, the petiolule, the bract, and the stipule of the new cultivar compared to 'Driscoll Agoura' and 'Driscoll Ojai'. This includes petiole length in centimeters, petiole diameter in centimeters, petiole pubescence, pose of hairs on the petiole, color of the petiole, color of the petiolule, petiolule length in centimeters, petiolule diameter in centimeters, bract frequency per petiole, stipule length in centimeters, stipule width in centimeters, stipule pubescence and stipule anthocyanin coloration.

TABLE 4

| Characteristic | 'DrisStrawEight' | 'Driscoll Agoura' | 'Driscoll Ojai' |
|---|---|---|---|
| Petiole length (cm) | 8.5 | 6.4 | 6.5 |
| Petiole diameter (cm) | 0.281 | 0.274 | 0.323 |
| Petiole pubescence | Very dense | Dense | Dense |
| Petiole pose of hairs | Outwards | Outwards | Between outwards to downwards |
| Petiole color | RHS 146C (Medium yellow-green) | RHS 146D (Medium yellow-green) | RHS 145A (Light yellow-green) |
| Petiolule color | RHS 146C (Medium yellow-green) | RHS 145A (Light yellow-green) | RHS 145A (Light yellow-green) |
| Petiolule length (cm) | 0.40 | 0.366 | 0.434 |
| Petiolule diameter (cm) | 0.145 | 0.131 | 0.194 |
| Bract frequency | 1 | 0 | 1 |
| Stipule length (cm) | 0.37 | 0.35 | 0.36 |
| Stipule width (cm) | 1.119 | 1.128 | 1.256 |
| Stipule pubescence | Absent/very sparse | Absent/very sparse | Medium |
| Stipule anthocyanin coloration | Weak | Weak | Weak |

Table 5 shows stolon characteristics of the new cultivar compared to 'Driscoll Agoura' and 'Driscoll Ojai'. These characteristics include the number of stolons, average number of daughter plants, the anthocyanin coloration of the stolons, the thickness of the stolons, and the pubescence of the stolons.

TABLE 5

| Characteristic | 'DrisStrawEight' | 'Driscoll Agoura' | 'Driscoll Ojai' |
|---|---|---|---|
| Stolon Number | Medium | Few | Many |
| Average number of daughter plants | 44 | 11 | 72 |
| Stolon Anthocyanin | Weak | Between weak and medium | Weak |
| Stolon Thickness | Thin | Between medium and thick | Medium |
| Stolon Pubescence | Absent or very sparse | Dense | Absent or very sparse |

Table 6 shows inflorescence characteristics of the new cultivar compared to 'Driscoll Agoura' and 'Driscoll Ojai'. These characteristics include inflorescence position relative to foliage, time of flowering, relative flower size, flower diameter in centimeters (measured from petal tip to petal tip), petal shape, relative spacing of petals, petal apex, base and margin, petal length in centimeters, petal width in centimeters, petal length to width ratio, number of petals, petal color, calyx diameter in centimeters (measured on back of flower from sepal tip to sepal tip), diameter of calyx relative to corolla, diameter of inner calyx relative to outer, sepal shape, apex and margin, sepal length in centimeters (measured from sepal tip to point of attachment to receptacle), sepal width in centimeters, number of sepals, receptacle color and anther color.

TABLE 6

| Characteristic | 'DrisStrawEight' | 'Driscoll Agoura' | 'Driscoll Ojai' |
|---|---|---|---|
| Inflorescence position relative to foliage | Above | Level with | Above |
| Time of flowering (50% of plants at first flower) | Early | Early | Early |
| Flower size | Medium | Medium | Medium |
| Flower diameter (cm) | 3.247 | 2.859 | 3.531 |
| Petal shape | Orbicular | Orbicular | Orbicular |
| Petal spacing | Overlapping | Overlapping | Overlapping |
| Petal apex shape | Rounded | Rounded | Rounded |
| Petal margin | Entire | Entire | Entire |
| Petal base shape | Concave-convex | Concave-convex | Concave-convex |
| Petal length (cm) | 1.741 | 1.577 | 1.818 |
| Petal width (cm) | 1.719 | 1.537 | 1.873 |
| Petal length/width ratio | 1.0-As long as broad | 1.0-As long as broad | 1.0-As long as broad |
| Typical and observed petal number | 6 | 7 | 6 |
| Petal color | RHS 155D (White) | RHS 155D (White) | RHS 155B (White) |
| Calyx diameter (cm) | 5.210 | 4.603 | 5.466 |
| Calyx diameter relative to corolla | Larger | Larger | Larger |
| Inner calyx diameter relative to outer | Same size | Larger | Same size |
| Sepal shape | Elliptical | Elliptical | Elliptical |
| Sepal apex shape | Convex | Convex | Retuse |
| Sepal margin | Entire | Entire | Entire |
| Sepal length (cm) | 2.174 | 1.814 | 2.103 |
| Sepal width (cm) | 0.897 | 0.766 | 1.031 |
| Typical and observed sepal number | 13 | 14 | 13 |
| Receptacle color | RHS 151B (Medium yellow-green) | RHS 151D (Medium yellow-green) | RHS 151B (Medium yellow-green) |
| Anther color | RHS 16B (Light yellow-orange) | RHS 14C (Light yellow-orange) | RHS 17A (Medium yellow-orange) |

Table 7 shows fruit characteristics of the new cultivar compared to 'Driscoll Agoura' and 'Driscoll Ojai'. These characteristics include fruiting truss length in centimeters, fruiting truss diameter, number of berries per truss, fruiting truss attitude, fruiting truss color, fruit length in centimeters, fruit truss width in centimeters, fruit length to width ratio, fruit hollow length and width in centimeters, fruit hollow length to width ratio, fruit weight in grams, relative fruit size, predominant fruit shape, difference in shape between primary and secondary fruits, band without achenes, unevenness of fruit surface, fruit skin color, evenness of fruit color, fruit glossiness, insertion of achenes, achene coloration (sunward and shaded sides of berry) and the number of achenes per berry.

TABLE 7

| Characteristic | 'DrisStrawEight' | 'Driscoll Agoura' | 'Driscoll Ojai' |
|---|---|---|---|
| Fruiting truss length (cm) | 17.4 | 14.4 | 16.7 |
| Fruiting truss length-general | Medium | Medium | Medium |

TABLE 7-continued

| Characteristic | 'DrisStrawEight' | 'Driscoll Agoura' | 'Driscoll Ojai' |
|---|---|---|---|
| Fruiting truss diameter (cm) | 0.295 | 0.297 | 0.348 |
| Number of berries per fruiting truss | 1 | 3 | 1 |
| Fruiting truss attitude | Prostrate | Prostrate | Prostrate |
| Fruiting truss color at base of truss | RHS 146C (Medium yellow-green) | RHS 145A (Light yellow-green) | RHS 145A (Light yellow-green) |
| Fruit length (cm) | 4.496 | 4.916 | 4.712 |
| Fruit width (cm) | 4.029 | 4.331 | 4.700 |
| Fruit length/width ratio | 1.1-As long as broad | 1.1-As long as broad | 1.0-As long as broad |
| Fruit hollow length (cm) | 2.216 | 2.532 | 3.032 |
| Fruit hollow width (cm) | 1.043 | 1.542 | 1.082 |
| Fruit hollow length/width ratio | 2.1 | 1.6 | 2.8 |
| Fruit weight (g) | 26.5 | 27.5 | 28.8 |
| Relative fruit size | Large | Large | Large |
| Predominant fruit shape | Conical and almost cylindrical | Almost cylindrical | Almost cylindrical |
| Difference in shape between primary & secondary fruits | None or very slight | None or very slight | None or very slight |
| Band without achenes | Broad | Medium | Medium |
| Unevenness of fruit surface | Weak | Weak | Medium |
| Fruit skin color | RHS 45B (Medium-red) | RHS 46A (Dark-red) | RHS 46A (Dark-red) |
| Evenness of fruit color | Even | Even | Even |
| Fruit glossiness | Medium | Medium | Weak |
| Insertion of achenes | Below surface | Level with surface | Above surface |
| Achene coloration-sunward side of berry | RHS 53B (Dark-red) | RHS 181A (Dark greyed-red) | RHS 182A (Dark greyed-red) |
| Achene coloration-shaded side of berry | RHS 146D (Medium yellow-green) | RHS 153A (Medium yellow-green) | RHS 152D (Medium yellow-green) |
| Achenes per berry | 200.8 | 331.4 | 174.5 |

Table 8 shows fruit characteristics of the new cultivar compared to 'Driscoll Agoura' and 'Driscoll Ojai'. These characteristics include the harvest maturity, insertion of calyx, pose of calyx segments, size of calyx in relation to fruit, adherence of calyx, firmness of flesh, color of the fruit flesh, evenness of the flesh color, distribution of flesh color, hollow center, sweetness of fruit, acidity of fruit, texture of fruit when tasted, type of bearing, grams of fruit per plant.

TABLE 8

| Characteristic | 'DrisStrawEight' | 'Driscoll Agoura' | 'Driscoll Ojai' |
|---|---|---|---|
| Harvest maturity | Early January to mid-June | Late January to mid-June | Late January to late May |
| Insertion of calyx | Set above fruit | Set above fruit | Level |
| Pose of calyx segments | Reflexed | Reflexed | Between spreading and reflexed |
| Size of calyx in relation to fruit | Larger | Between same size and larger | Larger |

TABLE 8-continued

| Characteristic | 'DrisStrawEight' | 'Driscoll Agoura' | 'Driscoll Ojai' |
|---|---|---|---|
| Adherence of calyx | Between medium and strong | Strong | Between medium and strong |
| Firmness of flesh | Firm | Firm | Extremely firm |
| Color of the flesh | RHS 155A (White) and RHS 41B (Medium-red) | RHS 155C (White) and RHS 41A (Medium-red) | RHS N155D (White) and RHS 45C (Medium-red) |
| Evenness of flesh color | Slightly uneven | Slightly uneven | Slightly uneven |
| Distribution of flesh color | Marginal and central | Marginal and central | Marginal and central |
| Hollow center | Large | Large | Large |
| Sweetness | Between medium and strong | Medium | Medium |
| Acidity | Medium | Medium | Medium |
| Texture when tasted | Medium | Medium | Medium |
| Type of bearing | Partially everbearing | Partially everbearing | Partially everbearing |
| Grams of fruit/plant | 529 | 617 | 504 |

Table 9 shows stress, pest and disease characteristics of the new cultivar compared to 'Driscoll Agoura' and 'Driscoll Ojai'.

TABLE 9

| Pest, Stress or Disease | 'DrisStrawEight' | 'Driscoll Agoura' | 'Driscoll Ojai' |
|---|---|---|---|
| High temperatures | Moderately resistant | | Moderately resistant |
| High pH | Moderately resistant | Moderately resistant | Moderately resistant |
| High soil salt levels | Moderately resistant | Moderately resistant | Moderately resistant |
| Water logging | Moderately resistant | | Moderately resistant |

TABLE 9-continued

| Pest, Stress or Disease | 'DrisStrawEight' | 'Driscoll Agoura' | 'Driscoll Ojai' |
|---|---|---|---|
| *Tetranychus urticae* | Moderately resistant | Moderately resistant | Moderately resistant |
| *Lygus hesperus* | Susceptible | Susceptible | Susceptible |
| *Botrytis* fruit rot | Moderately susceptible | Moderately susceptible | Moderately susceptible |
| Powdery mildew | Moderately resistant | Moderately resistant | Moderately susceptible |
| *Verticillium* wilt | Susceptible | Susceptible | Susceptible |
| Strawberry mottle virus | Moderately resistant | Moderately resistant | Moderately resistant |
| *Xanthomonas fragariae* | Moderately susceptible | Moderately susceptible | Susceptible |

COMPARISON WITH PARENTAL AND COMMERCIAL CULTIVARS

When 'DrisStrawEight' is compared to the male parent 'Driscoll Agoura' (U.S. Plant Pat. No. 15,731), 'DrisStraw Eight' begins fruiting a week to two weeks earlier than 'Driscoll Agoura'. Additionally, 'DrisStrawEight' is less rain tolerant and has smaller fruit size than 'Driscoll Agoura'.

When 'DrisStrawEight' is compared to the female parent 'Driscoll Ojai' (U.S. Plant Pat. No. 18,575), 'DrisStrawEight' begins fruiting two to four weeks earlier than 'Driscoll Ojai'. Additionally, the fruit of 'DrisStrawEight' is a lighter red and more conically shaped than the fruit of 'Driscoll Ojai'.

When compared to the commercial variety 'DrisStraw-Four' (U.S. Plant Pat. No. 19,240), 'DrisStrawEight' has a shorter petiole (8.5 cm) and higher fruit production (529 grams per plant), while 'DrisStrawFour' has a longer petiole (11.2 cm) and lower fruit production (443 grams per plant).

I claim:

1. A new and distinct cultivar of strawberry plant, as described and shown herein.

* * * * *